(12) United States Patent
Cowan

(10) Patent No.: US 9,314,347 B2
(45) Date of Patent: *Apr. 19, 2016

(54) METHOD AND IMPLANT DEVICE FOR GRAFTING ADJACENT VERTEBRAL BODIES

(71) Applicant: GLOBUS MEDICAL, INC., Audubon, PA (US)

(72) Inventor: John A. Cowan, Rome, GA (US)

(73) Assignee: Globus Medical, Inc., Audubon, PA (US)

( * ) Notice: Subject to any disclaimer, the term of this patent is extended or adjusted under 35 U.S.C. 154(b) by 323 days.

This patent is subject to a terminal disclaimer.

(21) Appl. No.: 13/853,241

(22) Filed: Mar. 29, 2013

(65) Prior Publication Data
US 2013/0317614 A1    Nov. 28, 2013

Related U.S. Application Data

(63) Continuation of application No. 13/366,890, filed on Feb. 6, 2012, now Pat. No. 8,425,606.

(60) Provisional application No. 61/499,271, filed on Jun. 21, 2011.

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/4425* (2013.01); *A61F 2/4465* (2013.01); *A61F 2/4611* (2013.01); *A61F 2002/2835* (2013.01); *A61F 2002/30062* (2013.01); *A61F 2002/3065* (2013.01); *A61F 2002/30224* (2013.01); *A61F 2002/30225* (2013.01); *A61F 2002/30227* (2013.01); *A61F 2002/30233* (2013.01); *A61F 2002/30446* (2013.01); *A61F 2002/30504* (2013.01); *A61F 2002/30509* (2013.01); *A61F 2002/30574* (2013.01); *A61F 2002/30576* (2013.01); *A61F 2002/30578* (2013.01); *A61F 2002/30607* (2013.01); *A61F 2002/30616* (2013.01); *A61F 2002/30662* (2013.01); *A61F 2002/30663* (2013.01); *A61F 2002/30665* (2013.01); *A61F 2002/30729* (2013.01); *A61F 2002/30777* (2013.01); *A61F 2002/30779* (2013.01); *A61F 2002/30785* (2013.01);
(Continued)

(58) Field of Classification Search
CPC ... A61F 2/4455; A61F 2/4465; A61F 2/4425; A61F 2002/443
See application file for complete search history.

(56) References Cited

U.S. PATENT DOCUMENTS

2003/0045877 A1* 3/2003 Yeh ........................... A61F 2/44
606/247
2003/0176925 A1* 9/2003 Paponneau ................. 623/17.16
(Continued)

*Primary Examiner* — David Bates
*Assistant Examiner* — Olivia C Chang

(57) ABSTRACT

A methodology for grafting together adjacent bony structures is provided using an implant device having an endplate with an inner disc portion and outer ring portion spaced from the inner disc portion by a connecting wall disposed therebetween. An endplate interior surface includes a retaining structure for securing the endplate to one of the bony structures, and endplate an exterior surface has an integrally formed socket. A ball-joint rod has a longitudinally extending body and an end, and at least a portion of the ball-joint rod end is curvilinear in shape. The curvilinear ball-joint rod end is rotatably disposed in the endplate socket to fixedly interconnect the bony structures.

19 Claims, 9 Drawing Sheets

(51) Int. Cl.
*A61F 2/28* (2006.01)
*A61F 2/30* (2006.01)

(52) U.S. Cl.
CPC ............ *A61F2002/30787* (2013.01); *A61F 2002/30789* (2013.01); *A61F 2002/30825* (2013.01); *A61F 2002/30841* (2013.01); *A61F 2002/30846* (2013.01); *A61F 2002/30863* (2013.01); *A61F 2002/30884* (2013.01); *A61F 2002/30891* (2013.01); *A61F 2002/30894* (2013.01); *A61F 2002/4475* (2013.01); *A61F 2310/00023* (2013.01)

(56) References Cited

U.S. PATENT DOCUMENTS

2006/0106381 A1\* 5/2006 Ferree et al. .................... 606/61
2006/0293755 A1\* 12/2006 Lindner et al. ............. 623/17.15

\* cited by examiner

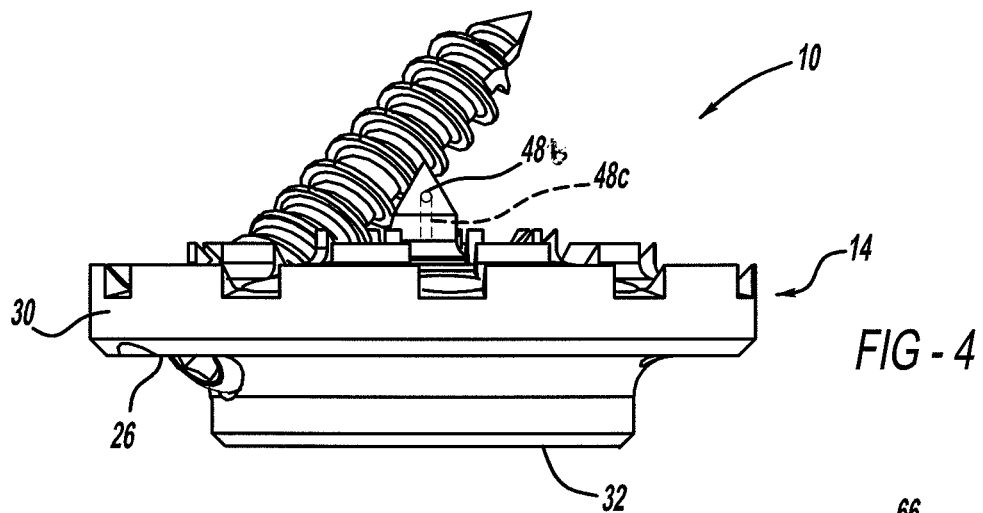
FIG - 4
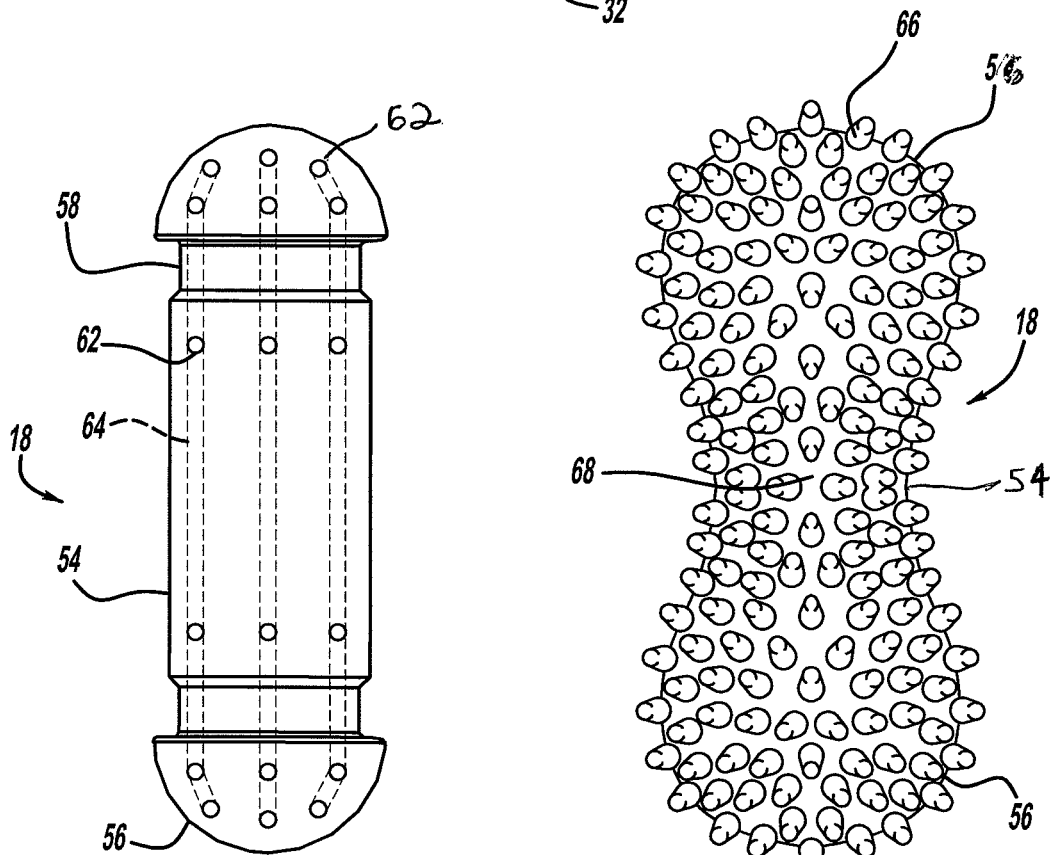
FIG - 5a
FIG - 5b

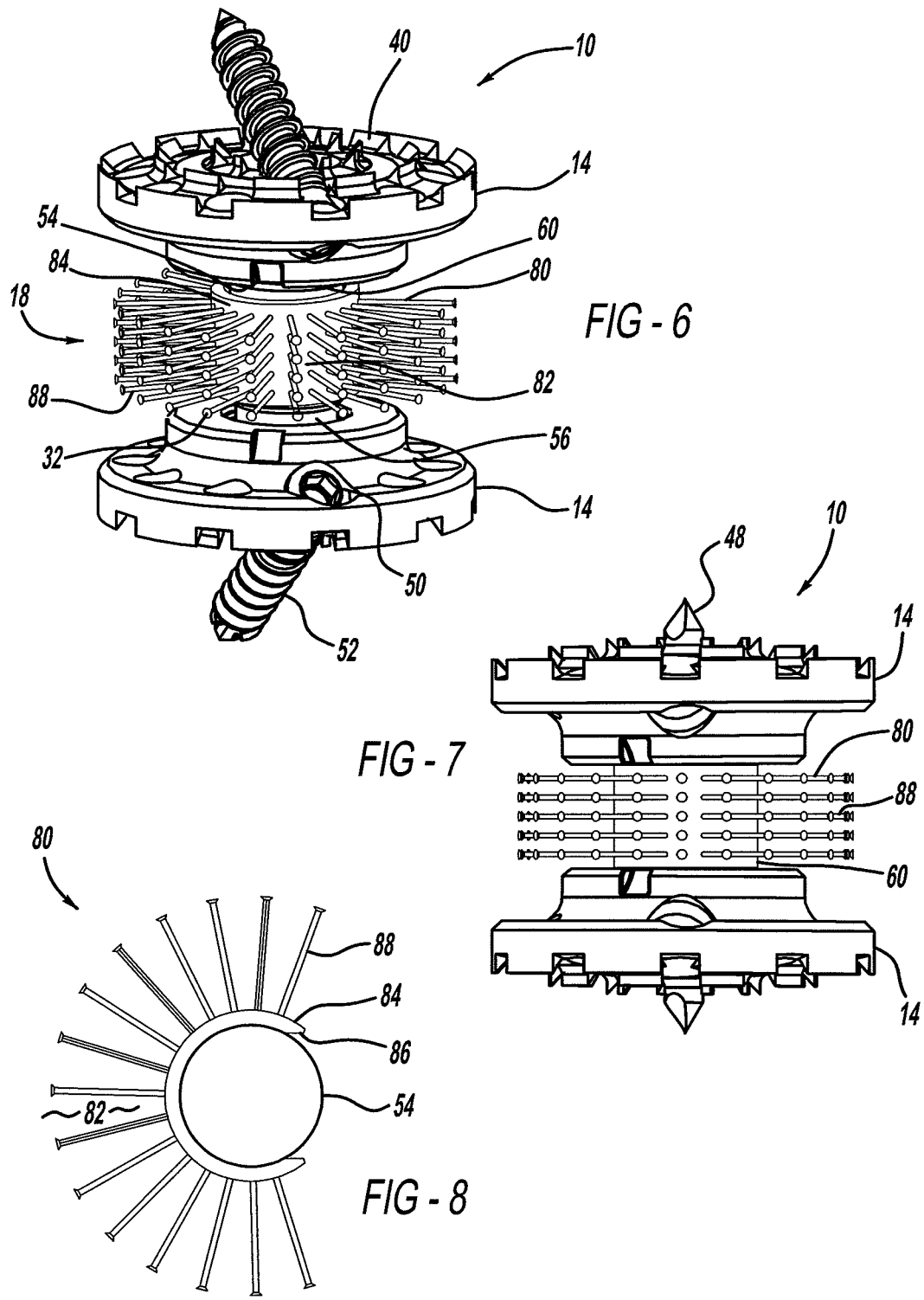

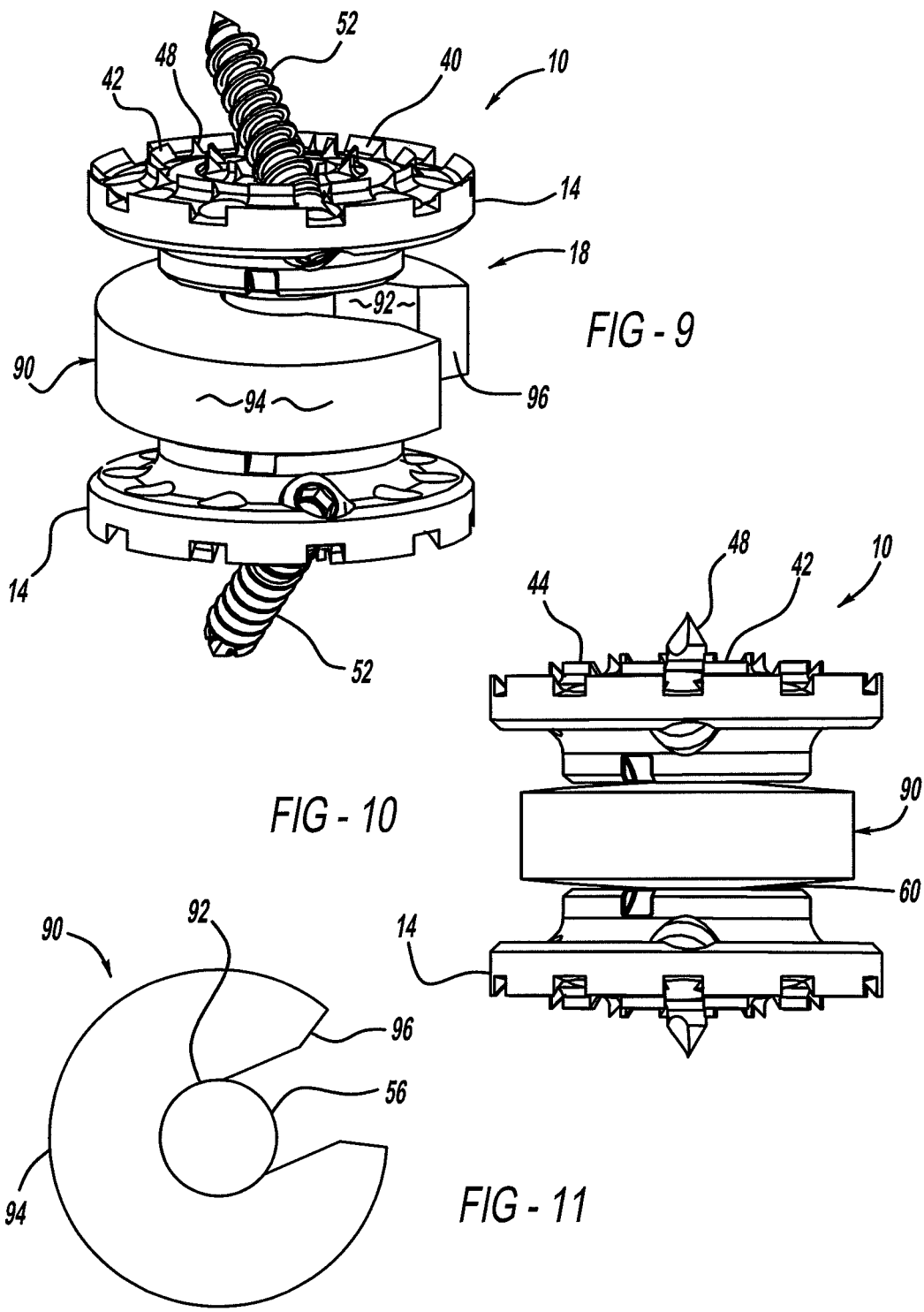

METHOD AND IMPLANT DEVICE FOR GRAFTING ADJACENT VERTEBRAL BODIES

CROSS REFERENCE TO RELATED APPLICATIONS

This application claims the benefit of and priority to U.S. Provisional Application No. 61/499,271, filed Jun. 21, 2011, winch is incorporated herein by reference.

BACKGROUND

The present disclosure relates generally to a vertebral implant device, and more particularly, to a method and implant device for grafting together adjacent vertebral bodies.

Diseases and injury to bone structures, such as the vertebral column, and conditions requiring surgical intervention are relatively common. A variety of conventional implant or graft devices are presently available for use in specific areas. The devices vary in size, shape, materials used, and insertion techniques. For example, in the vertebral column, grafts may provide restoration, decompression, or stabilization of the spine. Typically these devices include a member that is inserted in the vertebral column to replace an injured portion. An example of such a procedure is a corpectomy, which involves the replacement of a vertebral body with an implant or graft. The graft is secured to the adjacent vertebrae via a plurality of fasteners to maintain the position of the implant in situ.

While these conventional devices may generally provide adequate results, they have several disadvantages. For example, conventional graft devices utilized in a corpectomy procedure typically have a relatively bulky all-in-one construction and include several components. Such an implant construction limits surgery flexibility, including the approach to the spine. The instrument utilized for insertion is likewise limited due to the constraints of existing implant devices.

Thus, there is a need in the art for a graft device that has a modular construction such that components can be interconnected when and as needed to enhance surgery flexibility and offer increased adaptability to individual patent anatomy.

SUMMARY

Accordingly, the present disclosure relates to an implant device for grafting together adjacent bony structures. The implant device has an endplate with an inner disc portion and outer ring portion spaced from the inner disc portion by a connecting wall disposed therebetween. An endplate interior surface includes a retaining structure for securing the endplate to one of the bony structures, and endplate an exterior surface has an integrally formed socket. A ball-joint rod has a longitudinally extending body and an end, and at least a portion of the ball-joint rod end is curvilinear in shape. The curvilinear ball-joint rod end is rotatably disposed in the endplate socket to fixedly interconnect the bony structures. The methodology includes the steps of securing an endplate to each of the vertebral bodies and Interconnecting each endplate using a ball-joint rod.

One advantage of the present disclosure is that an improved implant device is provided that is modular in construction and enhances surgery flexibility allowing for minimally invasive approaches. Another advantage of the present disclosure is that the implant device is a vertebral graft that is easy to assemble and insert from a lateral or lateral extracavity approach. Yet another advantage of the present disclosure is that a vertebral implant device is provided that facilitates bone grafting. Still another advantage of the present disclosure is that the vertebral implant device includes a bristle post to help support bone growth. A further advantage of the present disclosure is that the vertebral implant device provides for strong and stable endplate gripping. Yet a further advantage of the present disclosure is that the vertebral implant device provides for modular in situ insertion for easier placement. Still a further advantage of the present disclosure is that the vertebral implant device provides for larger endplates which results in less "pistoning" and more aggressive distraction for enhanced performance. Still yet a further advantage of the present disclosure is that the vertebral implant device provides a snap-in ball-joint rod that enables variation in endplate alignment and angulation. Still yet another advantage of the present disclosure is that the vertebral implant device may include a snap-on bristle cage that enables generous and stable packing of bone graft. Still another advantage of the present disclosure is that the vertebral implant device provides may include a snap-on allograft strut. Yet another advantage of the present disclosure is that the vertebral implant device provides for motion preservation due to a ball-joint construct.

Other features and advantages of the present disclosure will be readily appreciated, as the same becomes better understood after reading the subsequent description taken in conjunction with the accompanying drawings.

BRIEF DESCRIPTION OF THE DRAWINGS

FIG. 4 is a side view of the endplate of the vertebral implant device of FIG. 3 including a fastener.

FIG. 5a is an elevational side view of a ball-joint rod of the vertebral implant device of FIG. 1.

FIG. 5b is an elevational side view of a ball-joint rod having a plurality of spikes, according to another embodiment.

FIG. 6 is a perspective view of a vertebral implant device having a bristle post fusion shall member.

FIG. 7 is an enlarged side view of the bristle post fission shaft member of FIG. 6.

FIG. 8 is a top view of the ball-joint rod and bristle shaft member of FIG. 6.

FIG. 9 is a perspective view of a vertebral implant device having a ring fusion shaft member.

FIG. 10 is an enlarged side view of the ring fusion shaft member of FIG. 9.

FIG. 11 is a top view of the ball-joint rod of FIG. 9.

DESCRIPTION

Referring to FIG. 1-20, an implant device 10 for use between adjacent bone structures is shown. In this example, the implant device 10 is a vertebral implant device 10 designed to be implanted in regions of the spine 12, such as the cervical, thoracic, and lumbar spine, although the location of implantation is non-limiting. For example, the vertebral implant device 10 can be used in the lateral extracavity, anterolateral, or direct anterior regions of the thoracolumbar spine to address indications relating to trauma, tumors, and degenerative issues such as scoliosis, or the like. The vertebral implant device 10 may serve as a modular mechanical graft to support eventual bone growth. The vertebral implant device 10 and its individual components can be fabricated from various materials, such as plastic, metal alloys, a bio-absorbable polymer, or the like, and the selection is non-limiting. The selected material may be magnetic resonance imaging (MRI) compatible. Implantation of the vertebral implant device 10 may be via lateral or lateral extracavitary approaches, in a manner to be described.

Figure 1:
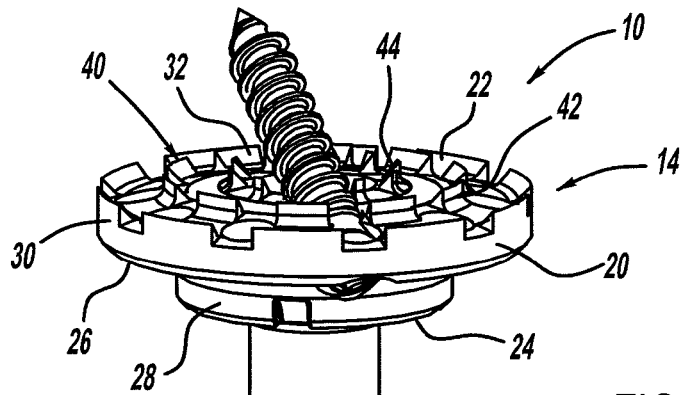
FIG. 1 is a perspective view of a vertebral implant device, according to an exemplary embodiment.
Figure 2:
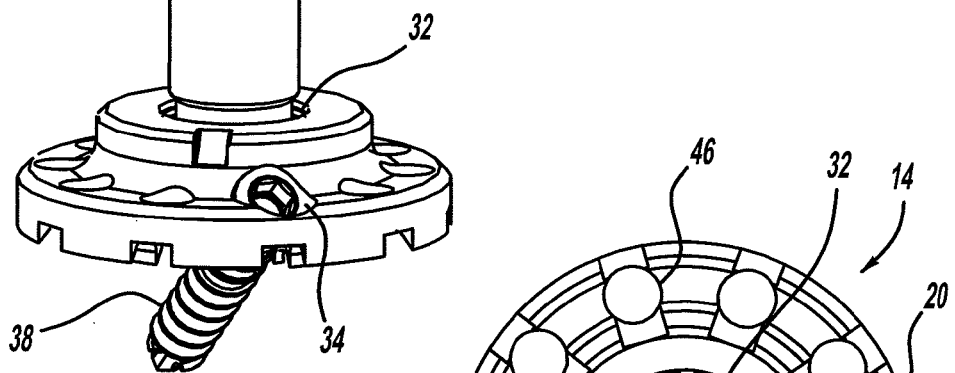
FIG. 2 is a top view of an endplate of the vertebral implant device of FIG. 1.
Figure 3:
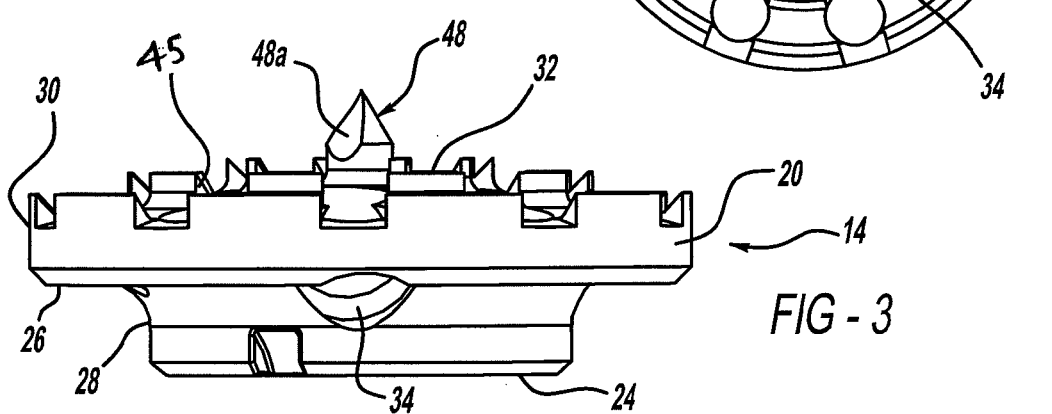
FIG. 3 is a side view of the endplate of the vertebral implant device of FIG. 2.

Referring now to FIGS. 2-4, the vertebral implant device 10 of this example is illustrated. The vertebral implant device 10 generally includes an endplate 14 that provides a direct attachment mechanism to the adjacent remaining vertebra 10 and distributes forces across the vertebra 16. In this example there is a first endplate 14 and a second endplate 14 that is spaced apart from the first endplate by a rod 18 or shaft. The endplate 14 may be about 5 mm thick and range from 20-40 mm in diameter. The endplate 14 can be made of various materials, such as titanium, PEEK, a bio-absorbable polymer, or the like. The endplate 14 includes an exterior surface 20 and an interior surface 22, and the endplate interior surface 22 is in direct contact with the adjacent vertebral body 16. The endplate interior surface 22 may have a variety of profiles, such as a concentric rings of varying thickness, or the like, to mimic anatomic doming of the vertebrae.

The endplate 14 has a generally circular disc-shaped profile. The endplate 14 includes an inner disc portion 24 that is spaced apart from a generally planar outer ring portion 26 by a connecting wall 28. A generally planar collar 30 extends away from an outer edge of the outer ring portion 26.

The endplate inner disc portion 24 is concave to form a socket 32 for receiving a portion of the ball-joint rod 18 in a manner to be described. The wall of the socket 32 may include apertures 34 so that bone marrow may pass therethrough from the passageways 36 formed within the vertebral implant device 10. Further, the wall of the socket may include another aperture (not shown) for receiving a locking set screw to prevent angular movement of the formed ball-socket joint from a final position. In another example, the wall of the socket 32 may include a structural formation, such as a circumferentially extending indentations, groves or the like, to facilitate grasping of corresponding spikes or protrusions on the ball joint rod end. This would allow gripping of the ball joint rod end at various angles but would prevent slipping from that predetermined angle, in a manner to be described.

The endplate 14 may also include a retaining structure 40 for securing the endplate 14 to the adjacent vertebral body 16. Further, the endplate 14 may include a plurality of retaining structures 40 that are concentrically arranged within the endplate interior surface 22 to form an inner ring wall. Additionally, the endplate 12 may include one or more concentric inner ring walls 42. Each concentric ring well 42 may have an increasing diameter to correspond to anatomic endplate surfaces of the adjacent vertebral bodies 16. An example of a retaining structure 40 is a cleat 44 extending outwardly from the endplate interior surface 22. Each cleat 44 may have a predetermined shape. In this example, cleat 44 has an upper surface that is angled/curved/actuate to conform to or mirror the dome- or bowl-like shape of the upper surface of the endplate. The cleat 44 may be hollow as shown at 45 to form another passageway 36 for bone grail material to travel through, and may connect with other passageways 36 formed in the endplate interior portion 22. The endplate 12 may also include a plurality of integrally formed apertures 46, and the apertures 46 may assume various shapes, such as circular or as a notch or the like. The openings formed between the retaining structures 40 similarly form a connection to passageways 36 that facilitate the transfer of bone growth therethrough.

Another example of a retaining structure 40 is a spike 48, such as a central spike as shown at 48a extending from the center of the endplate inner disc 24 for impactation into an object, such as the adjacent vertebral body 16 or the like. The central spike 48a can likewise have apertures 48b leading to art interior channel 48c to allow for autograft or bone marrow to seep through and support bone growth therein.

The endplate 12 also includes an opening 34 for receiving a fastener 38, such as a screw or the like, for either tacking or fixedly securing the endplate 14 to the adjacent vertebral body 16 or the like. In an example, the opening 34 is located in the endplate outer ring 26. If a temporary fixation of the endplate 14 to the anatomic endplate 98 of the adjacent vertebral body is desired, the fastener 38 may be a tack screw having a predetermined length, such as 3 mm. Similarly, the fastener 38 may be a screw having another predetermined length, such as 10 mm, although other types of fasteners 52 may be utilized.

Referring now to FIG. 5a, a ball-joint rod 18 that interconnects the endplates 14 and provides structural support to the removed vertebral body 16 is illustrated. The ball-joint rod 18 has a generally cylindrical body portion 54, with a first end 56 and an opposed second end 56. The ball-joint body portion 54 may vary in length depending on specific anatomical characteristics. The ball-joint body ends 56 each have a semi-spherical shape. Similarly, the ball-joint body end 56 may have a spherical shape, or a similar combination. The ball-joint end 56 is received in the socket 32 formed in the endplate 14, and thus corresponds in shape and dimension to mate with the endplate socket 32. For example, the ball-joint rod 18 may be between 5 mm to 30 mm in diameter.

Figure 20:
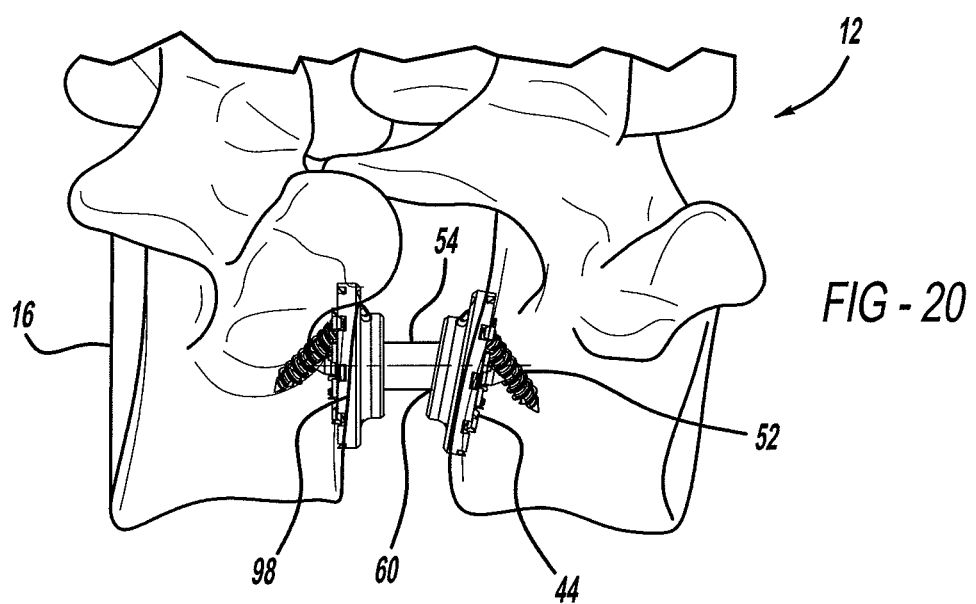
FIG. 20 is an elevational view of the vertebral implant device set at a predetermined angle.

The ball-joint rod 18 may also include other features, such as an integrally formed groove 58 positioned adjacent the ball joint end and extending circumferentially around the ball-joint body 54. The ball-joint rod groove 58 and the ball-joint body 54 operatively work in conjunction with each other to engage the socket 32 formed in the endplate 14 to create a snap-fit ball-joint 60 to retain the ball-joint rod 18 to the endplate 14. The ball-joint end 56 may be engaged in the end plate socket 32 using a variety of techniques, such as by using a spring loaded ring/washer, set screw, fastener, nitrite ring, or die like. For example, a locking device (not shown), such as a spring washer, may be inserted in the groove 58 to prevent the ball-joint rod 54 from disengaging from the endplate socket 32. The second ball-joint end, a second ball-joint groove and likewise are engaged with the socket formed in the second endplate to also create a snap-fit joint. This type of universal joint enables each of the endplates 14 to freely move independently from each other, as shown in FIG. 20. This flexibility enables variation in endplate alignment and angulation for improved insertion, attachment, and performance of the device 10. The ball-joint rod 14 body 54 can be of various sizes. In this example, the ball-joint body can range from 5 mm to 30 mm in length. The ball-joint rod body can be made of various materials, such as, titanium, PEEK, or the like.

The ball-joint rod 18 can also have a variety of other features to enhance performance, such as perforations, a hollow interior/core, extensions, spikes, or the like, to facilitate bone marrow growth and transit in, through, around passageways formed relative to the device 10. For example, the ball-joint end 56 may have apertures 62 connecting with passageways 36 extending through the endplate for transmitting bone marrow or graft material 82 therethrough passageways 64 formed in the ball-joint rod 18. Likewise, the ball-joint body 54 may have apertures 62 to connect with passageways 64.

In another example, an exterior surface of the ball-joint rod body 54 can have a plurality of outwardly extending spikes 66, as shown in FIG. 5*b*. The spaces between the spikes 66 may delineate channels 68 for bone growth. In an example, the spikes 66 can be arranged on the ball-joint rod end 56, such that the spikes 60 engage corresponding openings 34 in the endplates 12 to initially lock that ball-joint shaft into the endplate 14 at a selected position or angle 70. The ball-joint rod 18 can then be further locked in the selected position or angle by fasteners, such as screws, or the like.

Figure 19:
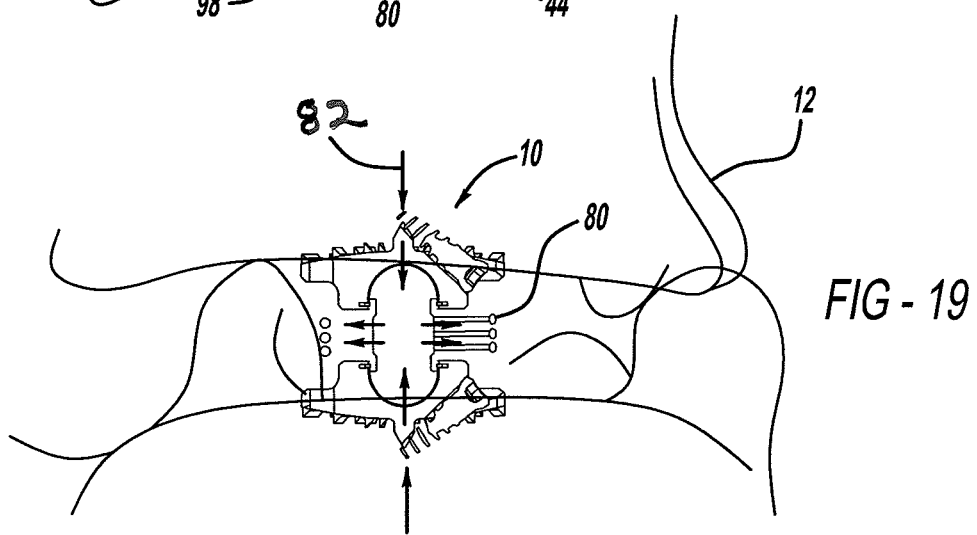
FIG. 19 is a sectional view of the vertebral implant device of FIG. 6 secured to two to adjacent vertebral bodies.

Referring now to FIGS. 6-8 the vertebral implant device 10 may include another member removeably attached thereto. In an example, the vertebral implant device 10 includes a fusion shaft member 80 that can be attached to the ball-joint rod body 54, and that acts as a carrier, support, and/or container for bone grafting tissue, bone growth, or the like. Examples of various potential pathways for bone marrow transit are depicted in FIG. 19 at 82. The fusion shaft member 80 has a circumferentially shaped body portion 84 that is placed over the ball-point shaft body 54. The fusion shaft member body portion 84 may have an opening 80 for engaging the ball-joint shaft body 54. The fusion shaft member body 84 also includes a plurality of extension members 88 or bristles that further facilitate bone growth and support of the graft. For example, the bristles 88 may contain a bone growth enhancement material such as allograft and/or autograft. The fusion shaft member 80 can have a variety of dimensions, sizes, shapes, or the like. In an example, the fusion shaft member 80 is a partial ring having a C-shape profile and having a circumference of approximately 270 degrees and includes a plurality of bristles extending outwardly therefrom, such as perpendicularly, or the like. The fusion shaft member 80 can be clipped in a snap-fit manner onto the ball-joint rod body portion. In another example, multiple fission shaft members 80 can be stacked adjacent to one another on the ball-joint rod body 54 for additional coverage and to help bind the joint. For example, the fusion shaft members 80 sway be positioned so that the opening of each is staggered. The fusion shaft member 80 can be made from a variety of materials, such, as, vicryl, PEEK, or the like. Similarly, the bristles 88 may be a microfiber material.

Referring now to FIGS. 9-11, another example of an additional member is illustrated. In this example, the vertebral implant device 10 includes a ring member 90, such as an allograft ring or strut, that can be attached to ball-joint rod body 54 to act as a carrier, support, and/or container for bone grafting tissue, bone growth, or the like. The ring member has an inner surface 92 that is placed adjacent to the ball-joint rod 54 and an outer surface 94 that further facilitates bone growth and support. The ring member 90 can have a variety of dimensions, sizes, shapes, or the like. In this example, the ring 90 has an opening shown at 96 to form a C-shaped profile, having a circumference of approximately 270 degrees and inferior and superior curvatures to span between the endplates. The ring member 90 can be clipped in a snap-fit manner onto the ball-joint rod body 54. Multiple rings 90 can be placed adjacent to each other on the bay-joint rod body 54, such as for additional coverage or to help bind the joint, or the like. The ring 54 can be made from a variety of materials, such as, vicryl, PEEK or the like.

Figure 12:
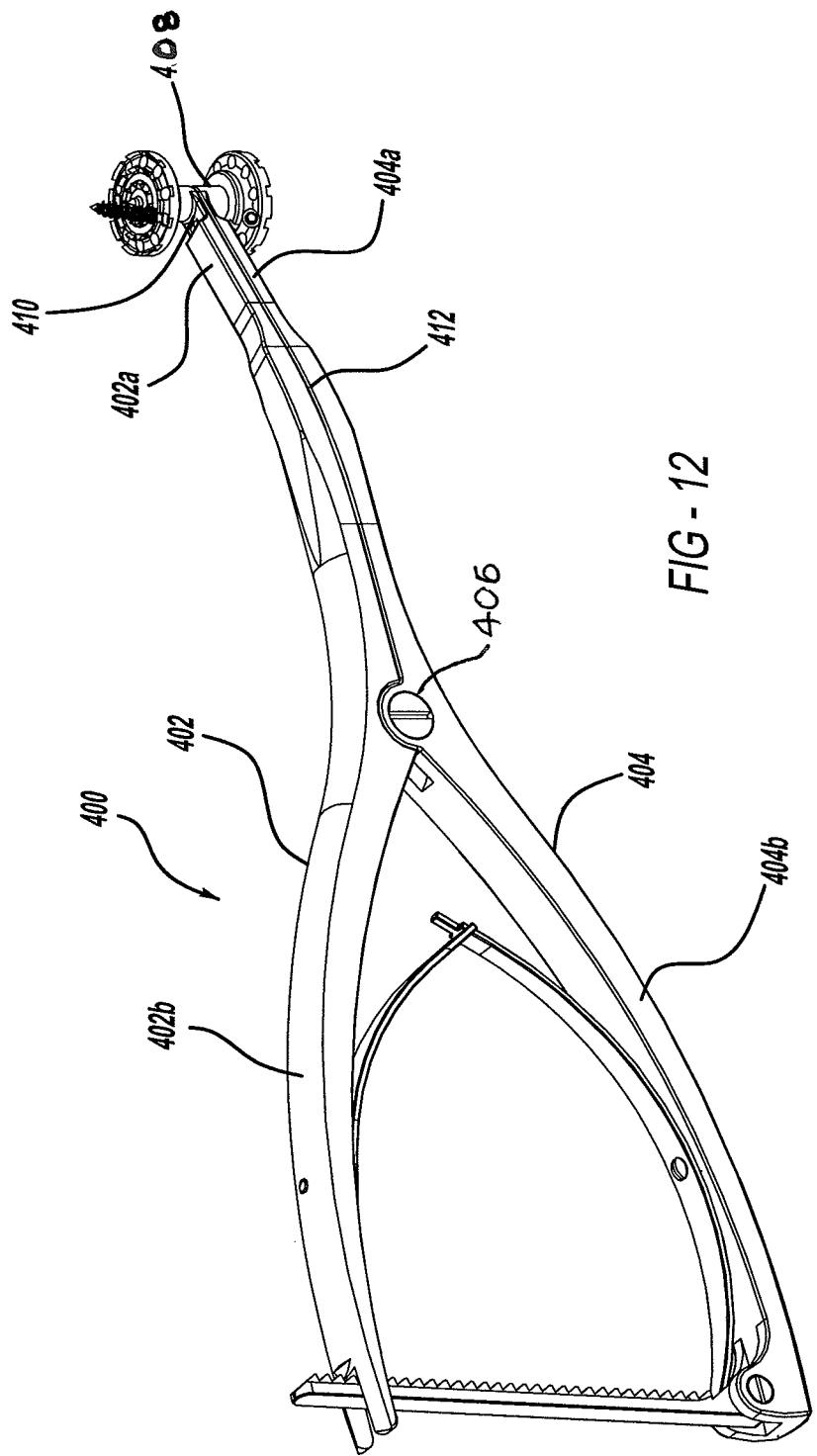
FIG. 12 is a perspective view of a device for inserting a vertebral implant into a vertebral region, according to an exemplary embodiment.

Referring now to FIG. 12, an insertion device 400 for implantation of the vertebral implant device 10 within the vertebrae 16 of a patient is shown. The insertion device 400 is generally Y-shaped and includes a first arm 402 having a first gripping portion 402*a* and a first handle portion 402*b*. The insertion device 400 also includes a second arm 404 having a first gripping portion 404*a* and a second handle portion 404*b*. The first arm and second arm 400, 404 are pivotably attached at a pivot point 406, above which defines the gripping portion and below which defines the handle portion. The arms 402, 404 move relative to each other in scissor-like fashion above the pivot point 406. The first arm and second arm gripping portion 408 operatively grips the vertebral implant device 10. The gripping portion 408 of the insertion device 400 includes a ball-joint 410 to mimic the ball-join shaft, while inserting the device 10. The insertion device 400 also includes a central guide member 412 for aligning and installing a fastener, such as a lock screw or the like. In operation, when the insertion device 400 is opened, the endplates 12 toggle on the insertion guide.

Figure 13:
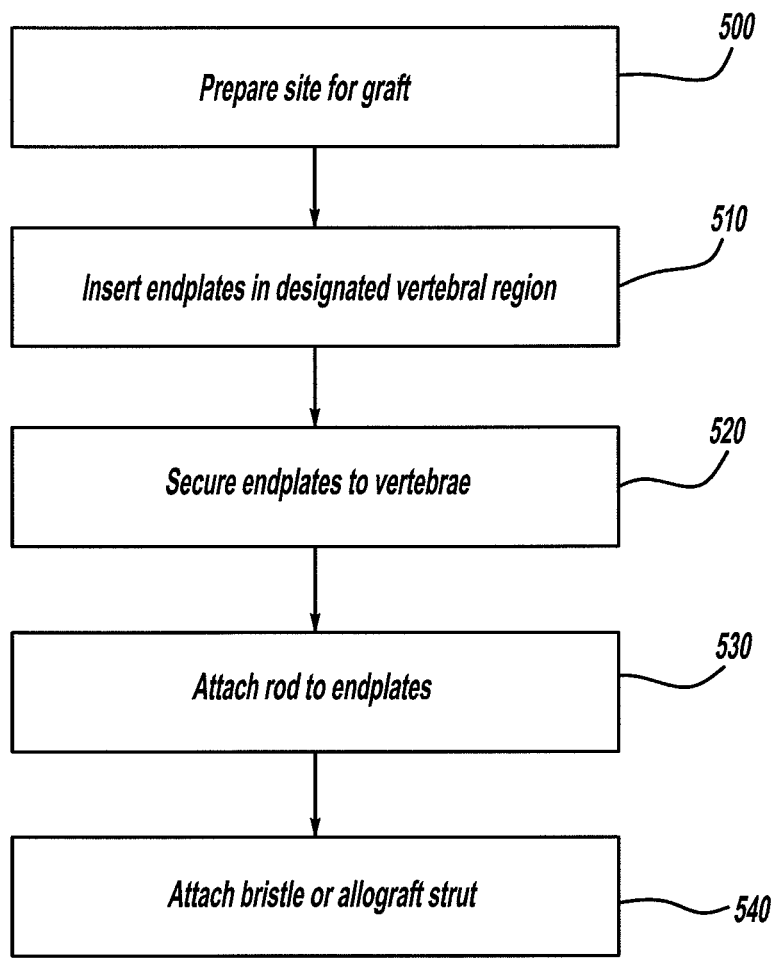
FIG. 13 is a flowchart of a method of inserting a vertebral implant device into a vertebral region, using the vertebral implant device of FIG. 1.
Figure 14:
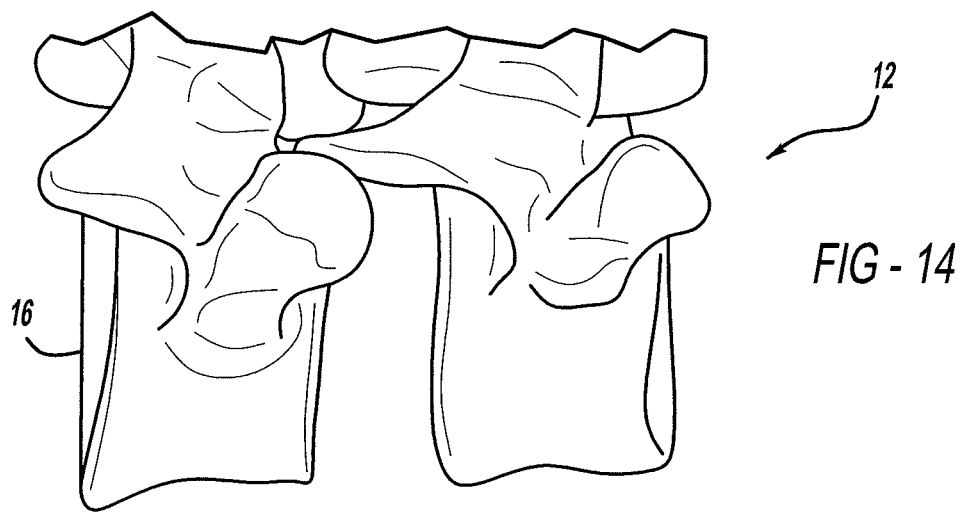
FIG. 14 is a side view illustrating a vertebral region having undergone a corpectomy according to the method of FIG. 13.

Referring now to FIG. 13, a flowchart outlining a method of implanting a vertebral implant device 10, such as in a corpectomy procedure, is illustrated. The methodology demonstrates the potential for hollowed components which would facilitate bone marrow or other bone matrix transit. The methodology begins in block 500 with the step of preparing the site for the graft. For example, a partial or complete corpectomy involving the removal of a vertebral body 16 or a portion of a vertebral body is performed on a patient. One or more vertebral bodies 16 may be removed, as shown in FIG. 14.

Figure 15:
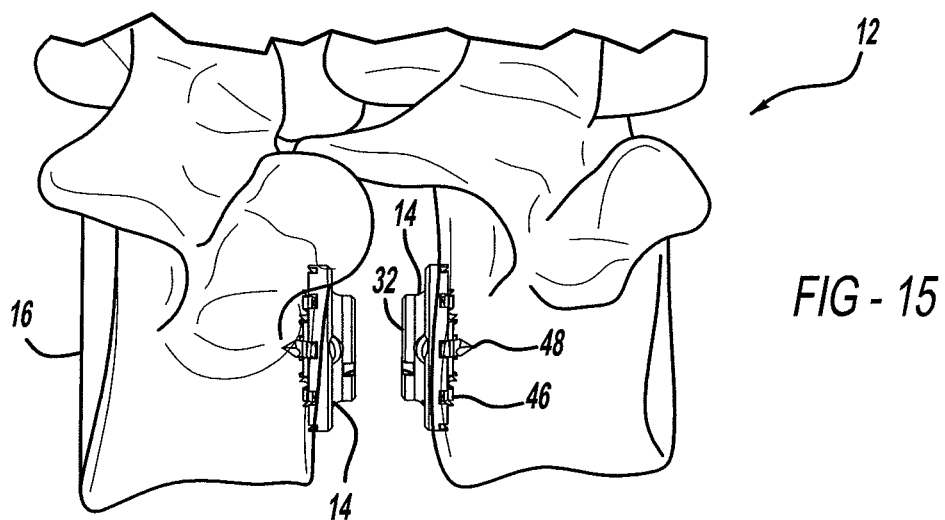
FIG. 15 is a side view illustrating a pair of endplates inserted between two vertebrae, according to the method of FIG. 13.

The method advances to block 510, which includes the step of inserting an endplate 14 onto an anatomic 98 endplate of an adjacent vertebral body 16. The size of the endplate 14 may be preselected using a gauge, such as an endplate sizer. Relevant dimensions include the diameter and length of the endplate 14. In this example, the insertion guide 400 is utilized to position the endplate 12 on the respective anatomic endplate 98. The first endplate and an opposed second endplate are positioned as shown in FIG. 15. The concentric inner rings 42 of the endplate 14 assist in the retention of the endplate 14 on the anatomic endplate 98. The retaining members, such as the centrally located spike 48 allows the endplate ring well 42 to be impacted into the anatomical endplate. Similarly, the cleats may also assist in temporarily tacking the endplate 12 in the desired position. As described, the interior portion of the endplate fits over the anatomic endplate 98, such as the cranial and caudal rings. A tack screw may be utilized to hold the endplate firmly against the vertebral body.

Figure 16:
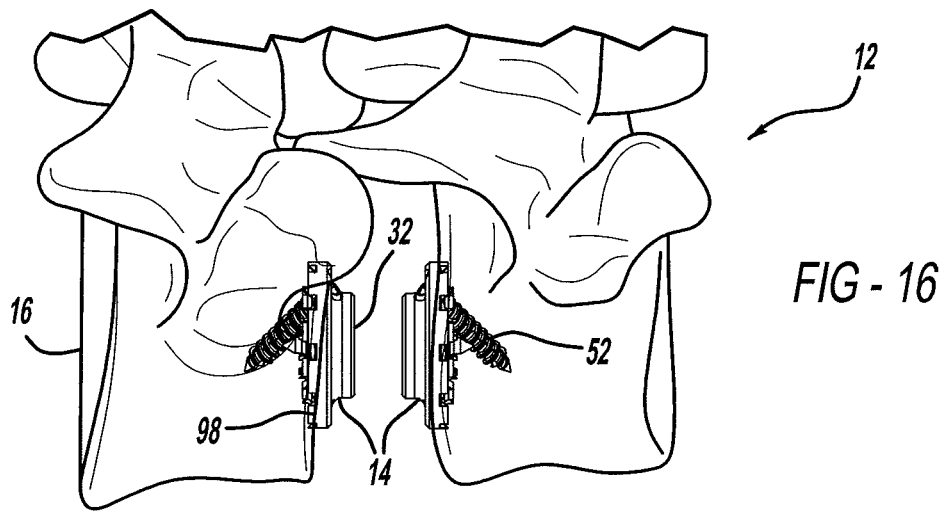
FIG. 16 is a side view of the endplates of FIG. 15 illustrating attachment of the endplates to the vertebrae.

The method proceeds to block 520 which includes the step of securing the first endplate and the second endplate to an adjacent vertebral body, as shown in FIG. 16. In this step, pilot holes can be drilled using the guide portion 412 of the insertion device 400 and screws placed therein while the insertion device 400 is holding the endplates 14 fixedly in position.

Figure 17:
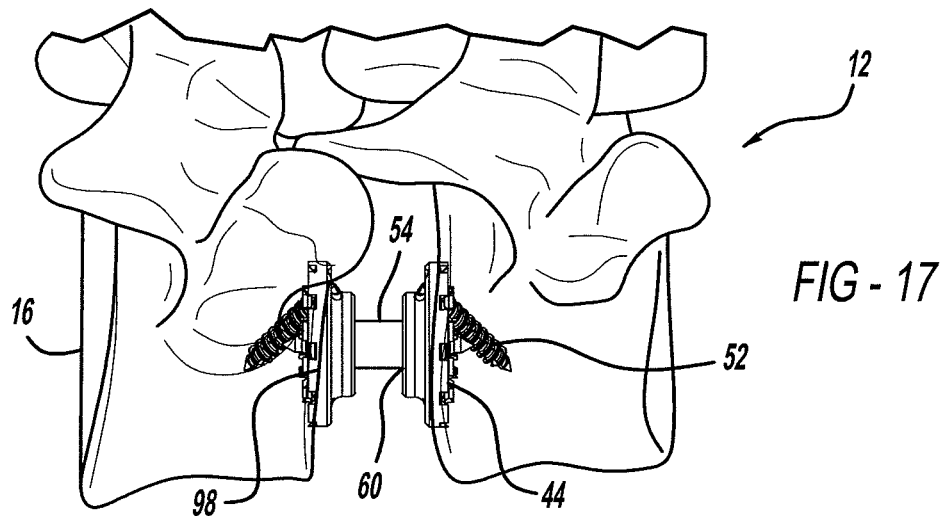
FIG. 17 is a side view illustrating attachment of a ball-joint rod to the endplates.

The method then proceeds to block 530 which includes the step of measuring the distance between the endplates, such as using a caliper. An appropriately sized ball joint rod 18 is selected and using the insertion device 100, the spherical ends 56 of the selected ball-joint rod 18 are disposed within the socket 32 formed in each endplate 14, as shown in FIG. 17. In this step, the ball-joint rod is snapped in position white the insertion device is over-distracting the endplates. The socket joint is open on one side to all the ball joints to facilitate snapping in place. The ball-joint rod 18 may be secured to the endplate 14. For example, a collar or groove portion 88 of the spherical end of the ball-joint rod may engage the socket 82 to form the ball and socket joint 60. The collar may be threaded to secure in place, or a lock screw, as previously described, may be utilized. The locking set screw may be utilized to keep the ball socket joint 60 from pivoting on implantation, until alignment is complete. If a ball-joint rod such as that described in FIG. 5b is utilized, that the relative angular position of the anatomical vertebral body with respect to the ball-joint rod may be set as shown in FIG. 20, such as by snap-fitting the bristle ends into a corresponding aperture in the socket. Advantageously, a positive fit is achieved and the snap-in fit makes assembly easier.

Figure 18:
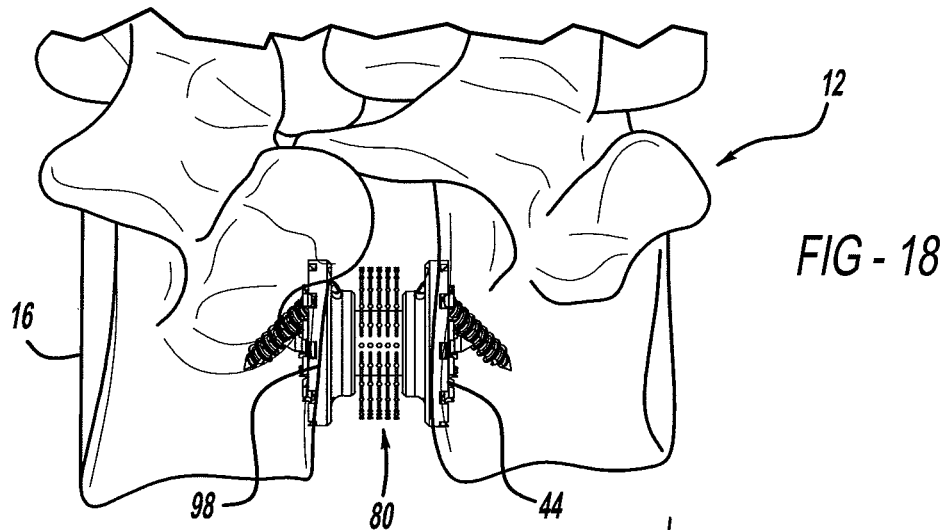
FIG. 18 is a side view of a bristle fusion shall member attached to the ball-joint rod of FIG. 17, according to an exemplary embodiment.

If it is desired to preserve the functionality of the joint, then the methodology ends. The ball and socket arrangement of the graft allows for relative movement of the adjacent vertebrae. If functionality of the joint is to be limited, the method proceeds to block 540 which includes the step of selecting and attaching a second member to the ball-joint rod. In an example, the mobility of the joint is limited using a locking screw as a cam to lock the angular position between the graft and an upper or lower vertebral body, such as between 15-20 degrees of angulation or the like. Further each endplate can be set at a different angle. In another example, a fusion member 80 such as a bristle post member and/or an allograft strut may be located onto the ball-joint rod body 54, as shown in FIG. 18. The bristle post member 80 may be snap fit onto the ball-joint rod body 54. These secondary devices promote bone growth around the graft, so that the adjacent vertebral bodies are fused together.

The method can be modified, in various manners, such as by adding steps, removing steps, rearranging steps, or the like. For example, the endplates may be further customized by heating the endplate and molding around the anatomical endplate to improve the bond therebetween. Advantageously, the device 10 may be assembly in situ and is readily customizable.

The present disclosure has been described in an illustrative manner. It is to be understood that the terminology which has been used is intended to be in the nature of words of description rather than of limitation. Many modifications and variations of the present disclosure are possible in light of the above teachings. Therefore, within the scope of the appended claim, the present disclosure may be practiced other than as specifically described.

What is claimed is:

1. An implant device for grafting together adjacent bony structures of a body comprising:
    an endplate having an inner disc portion and outer ring portion spaced from the inner disc portion by a connecting wall disposed therebetween, wherein an interior surface of the endplate includes a retaining structure for securing the endplate to one of the bony structures, and the endplate inner disc portion has an integrally formed socket;
    a ball joint rod having a longitudinally extending body and an end, wherein at least a portion of the ball-joint rod end is curvilinear in shape, and the curvilinear ball joint rod end is rotatably disposed in the endplate socket to fixedly interconnect the bony structures; and
    a fusion shaft member partially surrounding the body of the ball-joint rod, and the fusion shaft member includes a plurality of outwardly extending extension members.

2. The implant device of claim 1, wherein the fusion shaft member includes a body and the extension members are in the form of a plurality of bristles extending outwardly from the body.

3. The implant device of claim 1, wherein the fusion shaft member includes a body having a ring shape.

4. The implant device of claim 1, wherein the endplate includes a collar extending from an edge of the endplate outer ring.

5. The implant device of claim 1, wherein the endplate includes a passageway for transporting bone material therethrough.

6. The implant device of claim 1, wherein the endplate retaining structure is a centrally located spike protruding from the endplate interior surface.

7. The implant device of claim 1, wherein the endplate retaining structure is an inner ring wall protruding from the endplate interior surface.

8. The implant device of claim 1, further comprising a fastener for securing the endplate to the bony structure.

9. The implant device of claim 1, wherein the curvilinear ball joint rod end is semi-spherical in shape.

10. The implant device of claim 1, wherein the curvilinear ball joint rod end is spherical in shape.

11. The implant device of claim 1, further comprising a second endplate adapted to be secured to the adjacent bony structure, and the ball joint rod includes a second curvilinear ball joint rod end, each curvilinear ball joint rod end rotatably disposed in each endplate socket, to fixedly interconnect the bony structures.

12. The implant device of claim 9, wherein the endplate is fixed at a predetermined angle with respect to the ball joint rod body at a joint formed between the endplate and the ball joint rod.

13. The implant device of claim 1, wherein the endplate includes a plurality of apertures and a ball joint rod projecting member is disposed in the corresponding ball joint rod aperture.

14. The implant device of claim 1, wherein the ball joint rod includes a passageway for transporting bone material therethrough.

15. The implant device of claim 1, wherein the ball joint rod body includes a groove, and a retaining member is disposed in the groove to retain the ball joint rod end in the endplate socket.

16. The implant device of claim 1, wherein the bony structures are adjacent vertebral bodies.

17. An implant device for grafting together adjacent vertebral body structures of a spine comprising:
    an endplate having an inner disc portion and outer ring portion spaced from the inner disc portion by a connecting wall disposed therebetween, wherein an interior surface of the endplate includes a retaining structure and the endplate inner disc portion has an integrally formed socket, and the endplate is adapted to be secured to one vertebral body and another endplate is adapted to be secured to the adjacent vertebral body;
    a ball-joint rod having a longitudinally extending body and a first end and a second end, wherein at least a portion of each of the first ball-joint rod end and second ball-joint rod end is curvilinear in shape, and each of the curvilinear ball joint rod ends is rotatably disposed in the corresponding endplate socket to fixedly interconnect the vertebral bodies; and a fusion shaft member partially surrounding the body of the ball joint rod, and the fusion shaft member includes a plurality of outwardly extending extension members.

18. The implant device of claim 17, wherein the fusion shaft member includes a body and the extension members are in the form of a plurality of bristles extending outwardly from the body.

19. The implant device of claim 1, wherein the fusion shaft member is a partial ring having a C-shape profile configured to snap-fit onto the body of the ball joint rod.

* * * * *